(12) United States Patent
Yewdall et al.

(10) Patent No.: US 7,114,617 B2
(45) Date of Patent: Oct. 3, 2006

(54) CONTAINER

(75) Inventors: Gary Wayne Yewdall, Geelong (AU); Jillian Louise Isabel Mahon, Northcote (AU); Paul Murray Malouf, Airport West (AU); Mark Simon Bayly, Eltham (AU); Peter Kinglsey Bayly, Euroa (AU)

(73) Assignee: CSL Limited, Parkville (AU)

( * ) Notice: Subject to any disclaimer, the term of this patent is extended or adjusted under 35 U.S.C. 154(b) by 267 days.

(21) Appl. No.: 10/612,766

(22) Filed: Jul. 2, 2003

(65) Prior Publication Data

US 2005/0016887 A1 Jan. 27, 2005

Related U.S. Application Data

(60) Provisional application No. 60/394,008, filed on Jul. 2, 2002.

(51) Int. Cl.
*A61B 17/06* (2006.01)

(52) U.S. Cl. .................. 206/440; 206/565; 206/592

(58) Field of Classification Search ........ 206/438–441, 206/560, 565, 591–594; 220/216, 326, 221–227, 220/788, 795, 202, 203.01; 602/41, 48, 54
See application file for complete search history.

(56) References Cited

U.S. PATENT DOCUMENTS 3,679,088 A * 7/1972 Swett et al. ................. 220/789
3,997,677 A * 12/1976 Hirsch et al. ................ 206/484
5,127,523 A    7/1992 Herdlicka
5,293,997 A *  3/1994 Hustad et al. ............... 220/788
5,340,741 A *  8/1994 Lemonnier ............. 220/203.09
5,348,549 A *  9/1994 Brown et al. ................ 220/788
5,692,635 A   12/1997 Farrell et al.
5,984,137 A * 11/1999 Grosjean ..................... 220/795
6,189,717 B1 *  2/2001 Versaw et al. ............... 220/795
6,364,152 B1 *  4/2002 Poslinski et al. ........... 220/788

FOREIGN PATENT DOCUMENTS

WO    WO 99/59647    11/1999

* cited by examiner

*Primary Examiner*—Luan K. Bui
(74) *Attorney, Agent, or Firm*—Knobbe, Martens, Olson & Bear LLP

(57) ABSTRACT

A container for a relatively brittle product, such as a haemostatic bandage, including a body and a lid for closing the container to hermetically seal the product therein. A sealing rim of the lid includes a layer of elastomeric material which sealingly engages with a sealing rim of the container body to provide a first, static, seal and a second, dynamic, seal. The elastomeric sealing material extends into the interior of the container beneath the lid to provide an elastomeric formation operative to engage an upper surface of the product within the container so as to apply a resilient bias thereto to hold a lower face of the product against the base of the container. The elastomeric formation thereby acts to inhibit substantial movement of the product within the container.

41 Claims, 9 Drawing Sheets

CONTAINER

RELATED APPLICATIONS

This application claims the benefit of the U.S. provisional application 60/394008 filed Jul. 2, 2002 entitled "CONTAINER" which is incorporated herein in its entirety by reference.

BACKGROUND OF THE INVENTION

1. Field of the Invention

The invention relates to a container and more particularly, but not exclusively, to a container for a haemostatic bandage.

2. Description of the Related Art

International patent application WO99/59647 of The American National Red Cross, the disclosure of which is hereby incorporated by reference, relates to a haemostatic sandwich bandage for the treatment of wounded tissue and which comprises a plurality of layers that contain resorbable materials and/or coagulation proteins. Typical embodiments of the bandage as disclosed in this International application comprise a first fibrinogen layer, a thrombin layer adjacent the first fibrinogen layer and a second fibrinogen layer adjacent the thrombin layer. There may also be a layer of backing material on the side of the bandage opposite the wound-facing side, the backing layer being of a resorbable material or a non-resorbable material. Most practical applications of the bandage will incorporate the layer of backing material.

As disclosed in the International application as aforesaid, the bandage is fabricated by depositing successive layers of fibrinogen and thrombin into a mould to build up the sandwich with each layer being frozen after deposit prior to depositing of the next layer. After the sandwich has been assembled in this way, it is then freeze dried.

It will be appreciated that for all practical applications of this type of bandage, after freeze drying the bandage must be stored in a condition for use in a sealed package which will retain the product in a sterile state and which will also inhibit ingress of moisture. In its dried state the bandage is relatively brittle and for most practical applications the bandage will need to be packaged in such a way that it is physically protected against damage prior to use. Although the bandage has applicability in certain surgical procedures as may be performed in the operating room environment of a hospital, nevertheless a significant practical application is for the emergency treatment of wounds such as may arise in a military combat situation or a road traffic accident where immediate haemorrhage control is required to prevent mortality from exsanguination. When used in emergency treatment situations such as these, whether military or otherwise, the package is likely to be subject to rough handling but must still protect the bandage against breakage prior to use.

SUMMARY OF THE INVENTION

Aspects of the invention relate to a container for packaging a finished bandage to provide physical protection therefor against damage, and which, preferably, can also be used during the manufacture of the bandage. The container does however also have applicability to other products such as will be discussed subsequently.

According to one aspect of the invention, there is provided a container comprising a body and a lid for closing the container to hermetically seal a product therein, said lid having a sealing rim including a layer of elastomeric material which sealingly engages with a sealing rim of the container body, and said elastomeric sealing material extending into the interior of the container beneath the lid to provide an elastomeric formation operative to engage an upper surface of the product within the container so as to apply a resilient bias thereto to hold a lower face of the product against the base of the container.

According to another aspect of the invention, there is provided a container comprising a body and a lid for closing the container to hermetically seal a product therein, said lid having a sealing rim including a layer of elastomeric material which sealingly engages with a sealing rim of the container body, and said elastomeric sealing material extending into the interior of the container beneath the lid to provide an elastomeric formation operative to engage an upper surface of the product within the container so as to apply a resilient bias thereto to hold a lower face of the product against the base of the container, wherein the elastomeric formation acts to inhibit substantial movement of the product within the container, and the elastomeric formation flexes to accommodate a range of product thicknesses and/or surface irregularities.

According to yet another aspect of the invention, there is provided a container comprising a body and a lid for closing the container to hermetically seal a product therein, said lid having a sealing rim including a layer of elastomeric material which sealingly engages with a sealing rim of the container body, the sealing engagement providing a first, static, seal and a second, dynamic, seal and said elastomeric sealing material extending into the interior of the container beneath the lid to provide an elastomeric formation operative to engage an upper surface of the product within the container so as to apply a resilient bias thereto to hold a lower face of the product against the base of the container, wherein the elastomeric formation acts to inhibit substantial movement of the product within the container, and the elastomeric formation flexes to accommodate a range of product thicknesses and/or surface irregularities.

According to yet another aspect of the present invention, there is provided a container for a haemostatic bandage or other pharmaceutical product to protect the product against physical damage, said container comprising a body for housing the product and a lid for closing the container to provide a hermetically sealed enclosure for the product therein, said container having a facility for providing internal pressure relief over a substantial range of temperatures to permit maintenance of the hermetic seal throughout all temperatures to which the container will be expected to be exposed to.

Advantageously, in one embodiment, the pressure relief facility is provided by a deformable wall portion of the container body and/or lid.

In one particularly preferred embodiment of the invention, the deformable wall portion is provided in the lid and comprises a bellows-like flexible wall structure in the lid, preferably in a central part of the lid.

In a particularly preferred embodiment, the pressure relief facility is effective over a range sufficient to embrace sterilisation temperatures and also freezing temperatures. Such a temperature range is likely to extend to at least approximately 150° C. and possibly at least 180° C.

In the preferred embodiment, the body and lid are formed from a relatively robust semi-rigid polymer of pharmaceutical grade such as polypropylene and the hermetic seal between co-operating parts of the body and lid is formed by an elastomeric layer therebetween. Particularly advantageously, the elastomeric layer is applied to a peripheral rim of the lid to sealingly co-operate with a peripheral rim of the body.

In a preferred embodiment the sealing co-operation between the elastomeric layer and the peripheral rim of the body provides a first, static, seal and a second, dynamic, seal. The static seal preferably provides a locking action to releasably lock the lid to the peripheral rim of the container.

Particularly advantageously, when applied to a haemostatic bandage in addition to packaging the bandage for use, the bandage is at least partially manufactured within the container. Preferably, the bandage is subject at least to freeze drying within the container. To facilitate freeze drying with the lid applied to the container body but not sealed thereto, the container includes means for releasably locking the lid in a first position with its sealing rim raised from the sealing rim of the container body sufficient to enable withdrawal of moisture from the interior of the container during freeze drying. During this mode, the sealing rim of the lid is preferably uniformly spaced above the peripheral rim of the container body such that after freeze drying has been completed the lid can be pushed downwardly to release the locking force and to move its sealing rim downwardly into sealing engagement with the peripheral rim on the body or, conversely, the container body is able to be moved upwardly relative to the lid to achieve the same effect. It will be apparent that this facility is also of use for other pharmaceutical products at least partially manufactured within the container and subject to a freeze drying step.

Preferably, to provide effective heat transfer during freeze drying the outer surface of the container base is substantially planar to achieve large area surface contact with the surface of a freezing shelf of the freeze drier and hence to increase heat transfer.

Particularly advantageously, the container is of approximately rectangular shape and opening of the container is effected by co-operating lugs at one of the corner portions of the container, a first lug forming part of the lid and the second lug forming part of the container body with the two lugs being side by side such that opening can be effected by lifting the first lug while pushing down on the second lug to thereby raise the lid at the corner portion with further lifting pressure causing the sealing rim of the lid to progressively peal away from the sealing rim of the container body in directions towards the diagonally opposite corner portion. Particularly advantageously, a second set of such lugs is also provided at the diagonally opposite corner portion; the presence of this second set of lugs also permits an alternative opening method by raising the lid first at one corner portion in the manner defined above and then raising the lid at the other corner portion using the set of lugs at that corner portion whereby the lid can then be lifted from the container body.

According to another aspect of the invention, there is provided a container for use in the manufacture and subsequent packaging of a haemostatic bandage, said container comprising a body and a lid applicable to the body to hermetically seal the bandage therein, said body forming a mould for manufacture of the bandage by a deposition process into the body, with the product being freeze dried within the body prior to hermetic sealing closure of the container by the lid, wherein the container includes a retention system for releasably locking the lid in a freeze drying position in which the lid is closely adjacent to the body but is spaced from its hermetically sealed position such that moisture can escape between the container body and lid for freeze drying purposes and when freeze drying is complete, the lid can be moved into its hermetically sealed position.

Advantageously, the lid assumes the same orientation relative to the container body in its freeze drying position and its hermetically sealed position whereby movement from the freeze drying position to the hermetically sealed position involves a simple rectilinear movement of the lid relative to the container body.

In a particularly preferred embodiment, the lid is releasably retained in its freeze drying position by releasable locking lugs. Upon release of the locking effect provided thereby, the lugs also act to guide the lid into its hermetically sealed position. In the preferred embodiment, the lugs preferably depend downwardly from the lid for co-operation with a locking formation on the container body, the locking formation including a slot within which a lower end portion of each respective locking lug is received and through which the locking lug moves downwardly when the lid is moved from its freeze drying position into its hermetically sealed position, thereby guiding the lid.

Advantageously, the container also includes a facility to effect pressure relief within the interior of the container when hermetically sealed to compensate for pressure variation which will arise over a substantial range of operating temperatures including temperatures encountered on freeze drying. Preferably, the pressure relief facility is provided by a deformable wall portion of the body and/or lid, preferably the lid such as in the manner defined above.

The preferred embodiment also preferably has a sealing structure and/or an opening mechanism as defined above and preferably the sealing structure provided by the elastomeric sealing layer also extends inwardly of the container to apply a resilient bias to the surface of the bandage adjacent the lid to maintain the product resiliently held against movement within the container during use.

In a modification of this aspect, during freeze drying a part of the lid may be in sealing relation to the body with another part of the lid being releasably locked in a position to permit escape of moisture, and when drying is complete that latter part can then be moved into a position in which the container is hermetically sealed. This latter part may, for example, be formed by a part of the lid which is integrally hinged to the remainder of the lid and which is held in a raised position relative to the body during freeze drying to permit escape of moisture and when freeze drying is complete the hinged part can be lowered onto the sealing rim of the container body to complete the hermetically sealed closure.

According to yet another aspect of the invention, there is provided a method of manufacturing a haemostatic bandage comprising providing a container body which acts as a mould, forming the bandage within the mould by a deposition process, applying to the container body a lid in a first position in which moisture can escape between the container body and lid, freeze drying the product in the container body with the lid in the first position, and effecting relative displacement between the lid and container such that the lid is then in a second position in which the lid is hermetically sealed to the body so that the freeze dried product is hermetically sealed within the container.

Advantageously, in the first position the lid is releasably locked relative to the container body in the same orientation it assumes when its second position such that movement of the lid from its first position to its second position is a rectilinear movement relative to the container body in a downwards direction.

Advantageously, the undersurface of the base of the container body is made substantially planar for effective heat transfer with a freezing shelf during the freeze drying process.

Depending on the actual constituents of the bandage, one or more of the layers deposited within the mould formed by the container body may be frozen prior to deposition of the next adjacent layer such as described in International application WO99/59647. Although the bandage formed within the container is advantageously of the general construction described in that International patent application, the process is not restricted to haemostatic bandages in accordance with that International patent application.

Advantageously, the container used in the practice of the method in its preferred embodiments incorporates the various features defined above, either singularly or in combination. In particular, the container will at least comprise a pressure relief facility as defined above.

In a modification of this aspect of the invention, the bandage is formed or built within the container without the container needing to act as a mould.

In a further or alternative modification of this aspect, during freeze drying a part of the lid may be in sealing relation to the body with another part of the lid being in a position to permit escape of moisture, and when drying is complete that latter part can then be moved into a position in which the container is hermetically sealed. This latter part may, for example, be formed by a part of the lid which is integrally hinged to the remainder of the lid and which is held in a raised position relative to the body during freeze drying to permit escape of moisture, and when freeze drying is complete the hinged part can be lowered onto the sealing rim of the container body to complete the hermetically sealed closure.

BRIEF DESCRIPTION OF THE DRAWINGS

Embodiments of the invention will now be described by way of example only with reference to the accompanying drawings in which.

DETAILED DESCRIPTION OF THE PREFERRED EMBODIMENT

Figure 1:
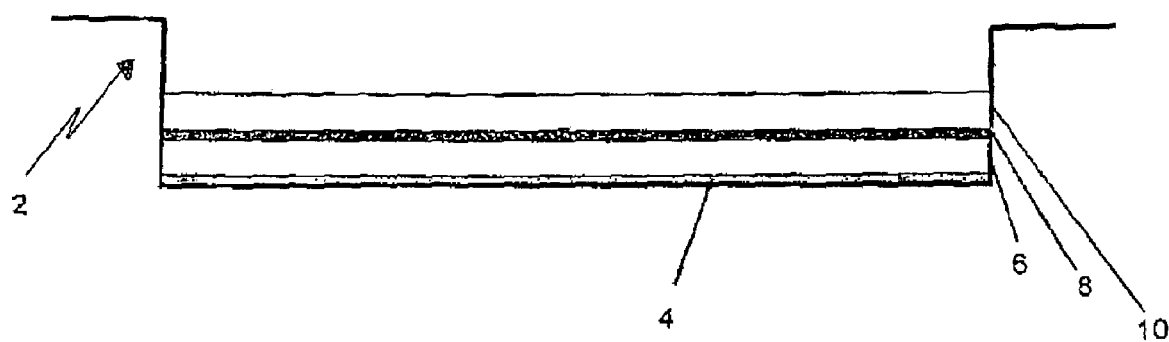
FIG. 1 is a schematic cross-section showing the body of a container in which a haemostatic sandwich bandage is formed.
Figure 2:
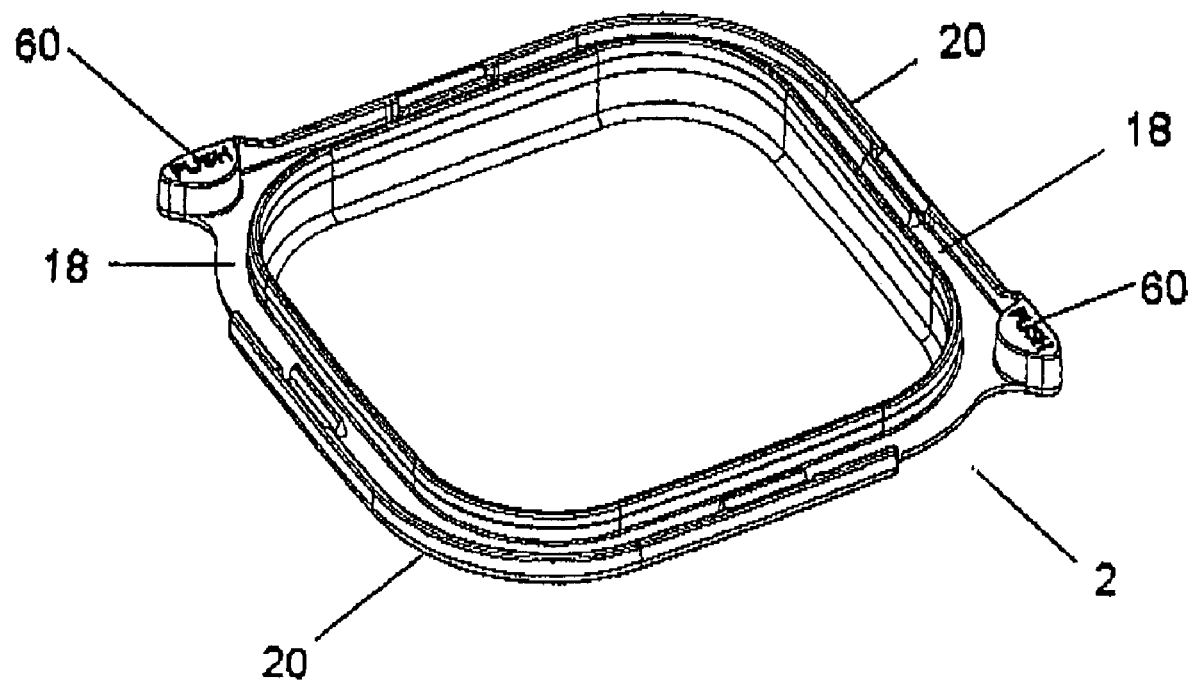
FIG. 2 is a top view showing the body of a container of a preferred embodiment of the invention.
Figure 2A:
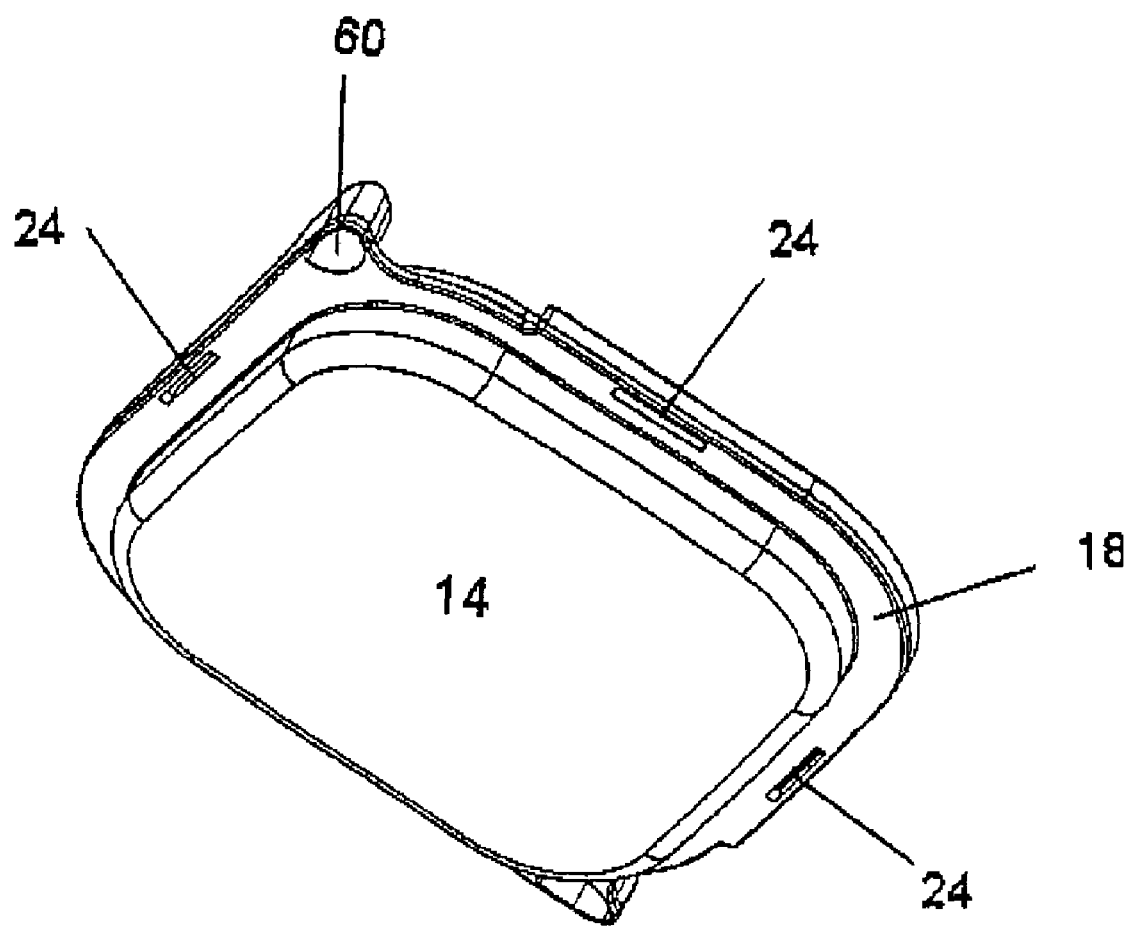
FIG. 2A is an underneath view of the container body shown in FIG. 2.
Figure 3:
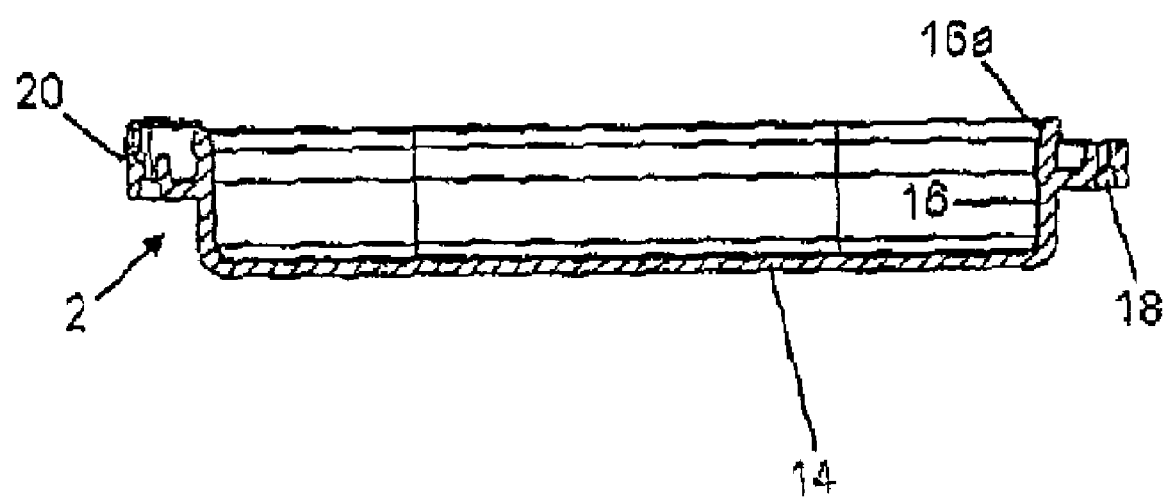
FIG. 3 is a cross-section through the container body.
Figure 4:
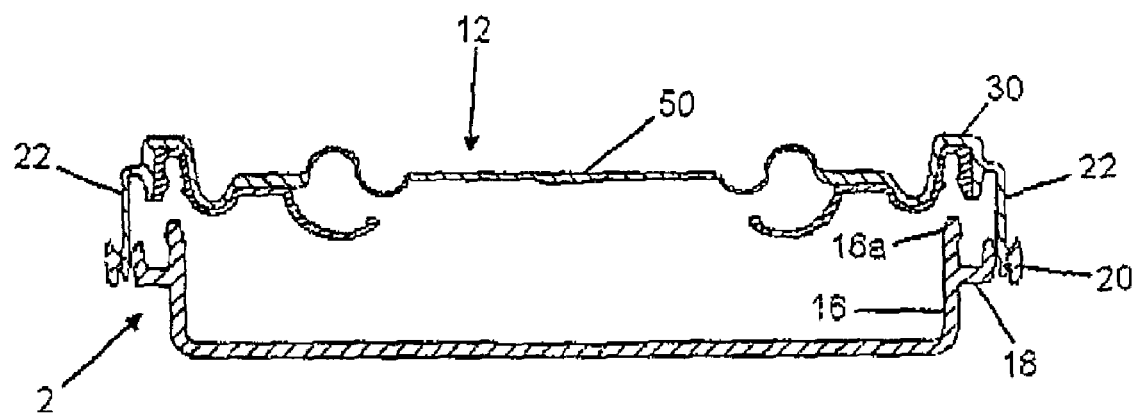
FIG. 4 is a cross-section showing the container body and co-operating lid applied thereto in a position to enable freeze drying of a haemostatic bandage formed in the container body.

FIG. 1 shows schematically the body 2 of a container for use as a mould in which a haemostatic sandwich bandage is formed and also one form of such a bandage within the mould. In the particular form shown, the bandage comprises a lower layer 4 of an absorbable bandage material and subsequent layers 6,8,10 comprising fibrinogen, thrombin and fibrinogen, the uppermost fibrinogen layer 10 being at the side of the bandage which will contact the wound. It is, however, to be understood that the invention is not restricted to the particular sandwich structure illustrated in FIG. 1 and the invention is equally applicable to haemostatic bandages of other structure, for example as disclosed in, but not restricted to, International patent application WO99/59647.

The layer 4 of absorbable bandage material, which constitutes the outer layer of the bandage in the embodiment shown, is placed on the upper surface of the base of the body 2 of the container and then the successive layers are deposited in fluid form with each layer being frozen prior to application of the next. During this process of building up the successive layers, the body 2 of the container acts as a basic mould to shape and confine the deposited material.

The preferred embodiment of the container is shown in greater detail in FIGS. 2 to 8 and comprises two parts, the main body 2 and a separate lid 12. As shown, the container is of substantially rectangular shape and of relatively shallow depth to accommodate the bandage. As will be apparent, the lid 12 is not present during the basic assembly steps of the bandage by deposition and freezing of the successive layers, but it is present during a freeze drying step as will be described.

The container body 2 and lid 12 are formed from a robust semi-rigid polymer such as polypropylene of pharmaceutical grade to provide effective physical protection for the bandage. The container body includes a base 14 and an upstanding peripheral wall 16 extending around the base 14. The upper edge portion of the peripheral wall 16 forms a sealing rim 16a which will be described in detail subsequently. A lateral flange 18 extends outwardly from the peripheral wall 16 and the flange 18 is bordered externally over a substantial part of its periphery by an upstanding peripheral rim 20. In one embodiment, the rim 20 is omitted in a zone adjacent two diametrically opposed corner portions for reasons which will be described subsequently.

It is traditional in a plastic container for the base of the container to have a slight concavity when viewed from the outside. This is normally of no consequence and usually arises as a result of mould design and mould flow conditions during moulding. In the container described, the base 14 of the container is on its external surface is substantially planar. This planarity is important during the production of the bandage as freeze drying after deposition into the container occurs by placement of the container on a freezing shelf and the planarity of the external surface of the base improves contact and hence heat transfer between the base and the freezing shelf during freeze drying of the assembled bandage. The means by which the planarity is achieved is by improving processing conditions for the chosen polymer, balancing mould temperatures between core and cavity, and careful balancing of the radial shrinkage with the cross-flow shrinkage of the polymer to remove/reduce moulded-in stresses.

The lid 12 of the container has a two-stage closure mechanism, the first stage maintaining the lid 12 in a partially open position relative to the body 2 during freeze drying (see FIGS. 4 and 5) and the second stage being a fully closed position providing a hermetically sealed closure after freeze drying so that the interior of the container is sealed against ingress of air and moisture (see FIGS. 6 and 7); in this second stage, the lid 12 holds the bandage within the container with a cushioning action to inhibit movement within the container and also shock damage. It will be apparent to those skilled in the art that a sealing system such as proposed will not provide a seal which is absolutely effective against total ingress of air and moisture over an infinite period of time. Rather, the hermetic sealing effect provided thereby is sufficient to preserve the product against degradation of the product by air and moisture over a predetermined useful "shelf life". In practice, the container will also be packaged within an outer pouch of foil or similar which further assists in providing a hermetically sealed environment for the product.

Figure 5:
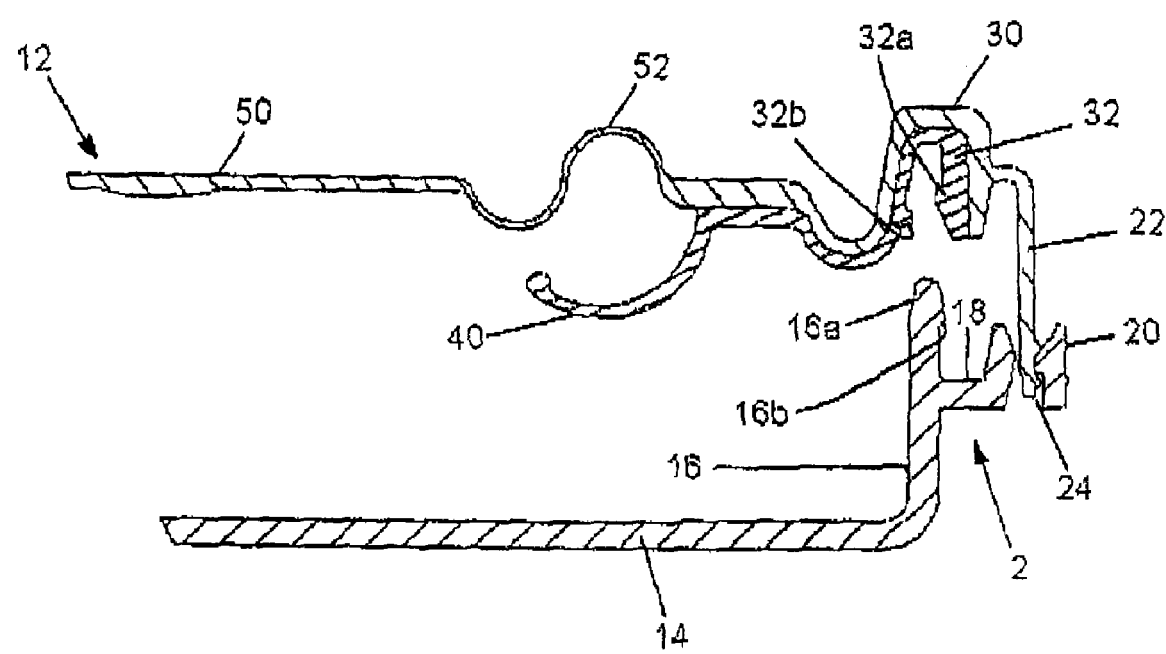
FIG. 5 shows a detail of FIG. 4 to an enlarged scale to better illustrate the co-operating between the lid and body.
Figure 6:
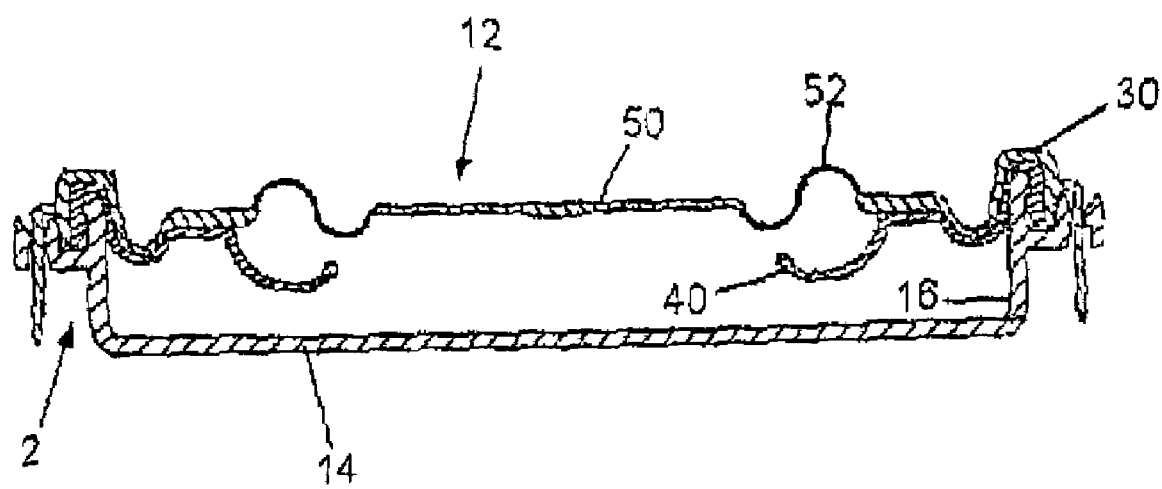
FIG. 6 is a section similar to FIG. 4 but showing the lid hermetically sealed to the body.

The first stage closure mechanism is provided by a series of legs 22 projecting downwardly from the outer peripheral rim of the lid 12. As shown, each of the legs 22 is positioned approximately midway along each of the four sides in the generally rectangular configuration illustrated, although other configurations are possible to achieve the same effect of holding the lid 12 in a partially open position. Each of the legs 22 is aligned with a corresponding slot 24 in the lateral flange 18 of the container body 2. The lower end portion of each leg 22 is shaped for releasable locking engagement with a lip formed on a part of the external rim 20 adjacent the slot 24 so that when the lower end portion of the leg 22 is seated within the slot 24 as shown in FIG. 5 there will be a releasable detent-type locking engagement between the leg 22 and the lip to ensure that the lid 12 is maintained in a raised condition relative to the sealing rim 16a of the container body 2.

After fabrication of the sandwich bandage in the manner previously described and prior to freeze drying, the lid 12 is applied to the container body 2 in the manner just described so that the lid 12 is held in its releasably locked partially open position. With the lid 12 thus positioned, the container can be placed in a freeze drier. Due to the partially open position of the lid in this mode, moisture from the product can escape. As soon as freeze drying has been completed, the lid 12 is moved downwardly into tight sealing engagement with the container body to inhibit rehydration. This is achieved by applying to the lid sufficient downwards force to release the detent locking effect exerted on the lower end portions of the legs 22 whereby the legs 22 can then displace downwardly through the slots 24 and a sealing rim 30 of the lid 12 will move into tight sealing engagement with the sealing rim 16a of the container body 2. Upon application of the downwards force to fully close the lid 12 onto the body 2 of the container, the movement of the legs 22 through the slots 24 also forms a guiding function to ensure that correct alignment is maintained between the sealing rim 30 of the lid 12 and the peripheral sealing rim 16a of the container body 2. It will be appreciated that the lid 12 moves downwardly with a rectilinear movement without change in the orientation between the lid 12 and the body 2.

Advantageously, the lower end portions of the legs 22 are tapered to provide an initial clearance fit relative to the corresponding slots 24 so as to facilitate initial location of the legs 22 relative to the slots 24 when applying the lid 12 to the base 2.

Figure 7:
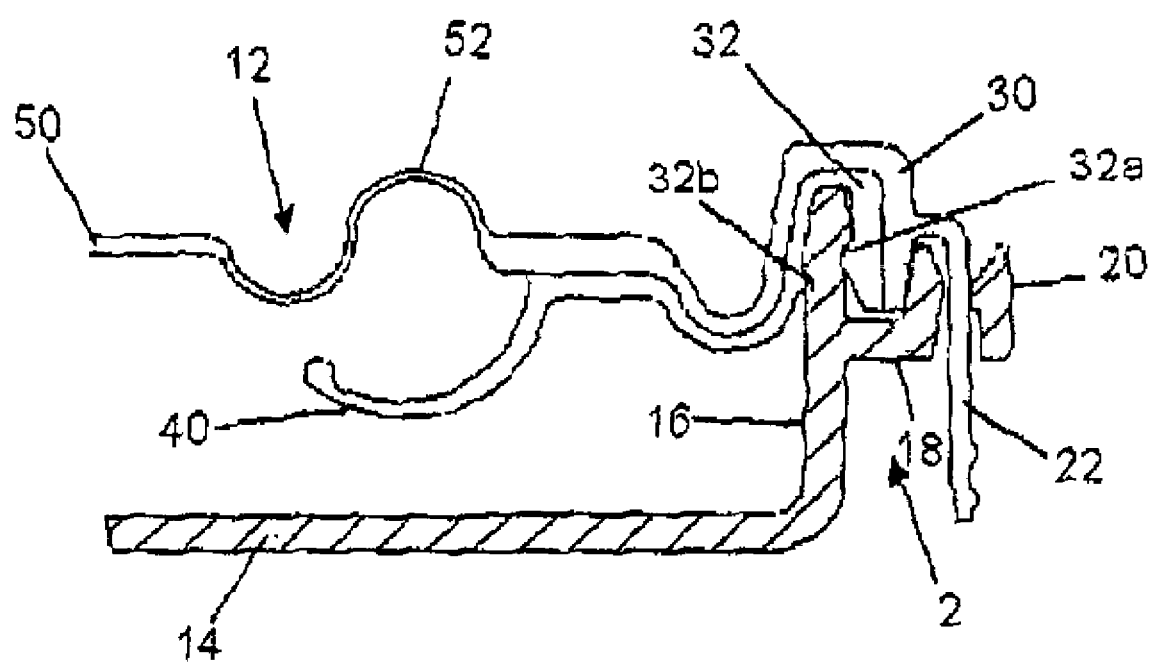
FIG. 7 is an enlarged view of a detail of FIG. 6 to better illustrate the sealing co-operation between the lid and body.
Figure 8:
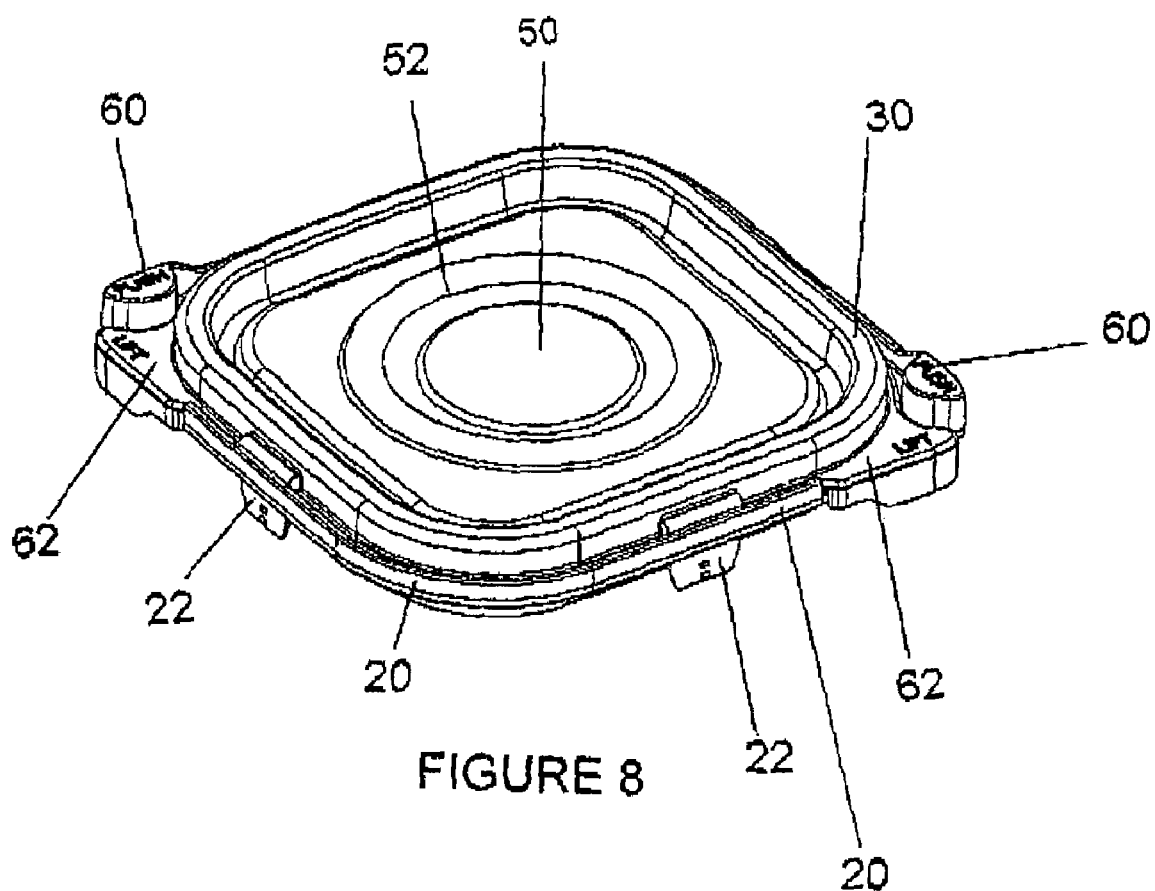
FIG. 8 is a perspective view showing the container with the lid hermetically sealed to the body.

The sealing rim 30 of the lid 12 is of inverted channel section. This receives a sealing insert 32 of a soft thermoplastic elastomer which is preferably moulded onto the lid 12 and co-operates with the sealing rim 16a of the container body 2 to provide a static and dynamic double seal. The static part of the double seal is provided by an inwardly-directed sealing lip 32a on the insert 32 which positively locks beneath and seals against an outwardly-directed lip 16b on the sealing rim 16a of the container body 2. The dynamic part of the double seal is provided by a sealing rib 32b on the insert 32 and which projects outwardly to engage sealingly the inner surface of the sealing rim 16a. The co-operation between the insert 32 and sealing rim 16a is best illustrated in FIG. 7. Due in part to the sealing application of the lid 12 immediately following the freeze drying process and also due to a subsequent sterilisation step, the lid 12 is subject to a very wide temperature variation and some deflection is bound to arise. Such deflection will be accompanied by sliding movement of the sealing rib 32b along the inner face of the sealing rim 16a thereby accommodating the deflection due to temperature variation but without destroying the integrity of the double seal. A further sealing zone is formed between the upper end edge of the sealing rim 16a and the immediately adjacent surface of the sealing insert 32.

In the fully closed position of the lid 12, the lid 12 is positively, but releasably, locked to the container body 2 by the interengagement of the lips 16b, 32a. If required, a further positive, but releasable, locking action can be provided by locking interengagement between the upper part of the legs 22 and the rim 20; this additional positive locking action is not present in the embodiment particularly described.

During closure of the lid 12 interaction between the outer side of the slot 24 and the outer surface of the leg 22 applies an inwards force which tends to push the sealing lip 32a into locking engagement with the lip 16b. It is also to be noted that the sealing rim 16a is tapered. This ensures that the dynamic seal does not become properly effective until there is substantial engagement between the sealing rims 16a and 30 to thereby minimise the amount of air entrapped within the sealing structure during closure.

The elastomeric sealing insert 32 extends inwardly along the underside of the lid 12 from the sealing rim to terminate in a ring-shaped formation 40 of approximately donut-like form. This is located within a central part of the lid at the underside thereof and at a height to engage the upper surface of the bandage and to apply a resilient bias thereto to hold the bandage against the base 14 of the container to thereby inhibit any substantial movement of the bandage within the container throughout all anticipated operating conditions and which might otherwise result in damage to the relatively brittle bandage, even if the container is subjected to certain forms of shock loading as may arise in a military environment. The donut formation 40 will also flex to accommodate a range of thicknesses of the bandage and/or surface irregularities of the bandage.

Following closure of the lid 12 after freeze drying to seal the bandage within the container, the container is then heated to a temperature of in excess of 100° C. for sterilisation purposes. Given that the container is likely to be subject to a temperature of between approximately −50° C. and −80° C. during processing, the sealed container will be subject to a temperature range of at least 150° C. To accommodate the varying internal pressures which will arise over this extreme range of operating temperatures, a central part 50 of the lid 12 is connected to the outer part via a thin-walled annular zone 52 of serpentine cross-section which acts in the manner of a bellows to permit deflection of the central part 50 relative to the outer part consequent on internal pressure variation to relieve the pressure variation and to thereby ensure that the integrity of the seal is maintained.

Advantageously, the central part 50 of the lid 12 is positioned below the level of the sealing rim 30 so that when the lid 12 is closed onto the body 2 after freeze drying and which occurs by lowering of a plate onto the lid 12 to press the lid 12 downwardly by engagement with its sealing rim 30, the central part 50 will be able to rise sufficiently to effect pressure relief of the entrapped air, thereby avoiding the need to remove that air. The lid 12 can be closed under a slight vacuum to ensure that the central part 50 returns to a neutral position when removed from the environment of the freeze drier.

In use, the container is likely to be subjected to an expected operational temperature range of from −60° C. to +60° C. and it will be apparent that the pressure relief function is effective throughout this operational range to ensure that the integrity of the seal is maintained until the container needs to be opened to access the product.

In an alternative embodiment, the sealing insert 32 is extended across the entire dimension of the lid and a very small opening is provided off-centre in the central part 50 of the lid to allow the pressure variations to be taken by the elastomeric insert 32 but with all mechanical protection being provided by the central part 50 of the lid (other than at the very small opening).

In another alternative embodiment, the central part 50 of the lid may be omitted and the elastomeric sealing insert 32 is extended across the entire dimension of the lid 12. The central part of that insert is then able to deflect to accommodate the internal pressure variation over the extreme temperature range encountered. While this alternative configuration can be used in more controlled environments such as hospitals where the container is not likely to be subject to rough handling, in a container for use in a military or similar emergency environment the exposure of the elastomeric sealing insert will not be acceptable as it is too susceptible to damage and for those environments a configuration such as is illustrated in which the elastomeric sealing insert is enclosed by the outer more robust layer of the lid is preferred.

In practice it is also desirable for the container to have a certain degree of transparency after closure of the lid for final inspection of the bandage to ensure that no significant physical damage has occurred during processing as evidenced by the presence of visually observable cracking or breakage of the relatively brittle bandage.

After sterilisation, the container is sealed within an outer or secondary pouch of foil or similar to maintain sterility and also to assist in excluding air and moisture.

The sealing mechanism particularly described, in which the sealing rim 30 of the lid 12 is positively locked to the sealing rim 16a of the container body 2 by the static seal which acts in conjunction with the dynamic seal, ensures that the lid 12 is firmly applied to the container body 2 such that accidental removal cannot occur even under harsh conditions. The outer rim 20 externally of the flange 18 acts to shield the outer edge portion of the lid 12 in its fully closed position to form a barrier to externally-applied forces which might result in accidental opening of the container.

The flange 18 provides effective lateral stiffening to the sealing rim 16a so that the sealing rim will not deform under the sealing forces and forces applied to the container during handling to thereby ensure that the sealing effect is preserved. Also, the flange 18 reduces shrinkage during moulding of the container body 2 to ensure that the required shape of the sealing rim 16a is preserved to ensure effective sealing.

In addition to the shielding function provided by the outer rim 20 as just discussed, it also acts to protect the sealing lip 16b from accidental damage by external objects contacting the lip during moulding of the base 2 and during subsequent handling such as transport and assembly to the lid 12. It also acts as a bumper strip which can engage the rim 20 of an adjacent container during processing so that successive containers can be pushed along a production line without adjacent containers riding up, one over another.

Although it is necessary that the lid 12 is firmly applied to the container body 2 such that accidental removal cannot occur even under harsh conditions, nevertheless it is important that when the bandage is required for use, the container is able to be opened quite easily. In the case of a combat injury for example, the container may need to be opened either by the injured person or a colleague, either of which are likely to be suffering from trauma with shaking hands. To facilitate opening in very stressful situations such as these, an opening mechanism is incorporated at each of two opposed corner portions of the container. Each opening mechanism comprises a rigid lug 60 on the container body 2 as an extension of the outer rim 20 and a rigid lug 62 on the lid 12 as an extension of the sealing rim 30 thereof. The lugs 60,62 are in side-by-side relation. The rigid lug 62 on the lid 12 extends across the flange 18 on the body 2 into the zone where the outer rim 20 is absent, the lug 62 extending downwardly to a level beneath the lower edge of the lug 60 on the container body as clearly illustrated in FIG. 8. This differential height facilitates location of the thumb and forefinger of a hand onto the respective lugs 60,62 just by feeling the lugs as may be necessary in darkness or if the sight of the personnel is impaired, and by pushing downwardly on the body lug 60 and upwardly on the lid lug 62 the lid 12 will be lifted away from the sealing rim 16a at that corner portion as a result of the inherent rigidity of the lid 12 and body 2 in the corner portion. Progressive lifting of the lid 12 from the corner portion will cause the remainder of the sealing rim 30 of the lid 12 to progressively peel away from the peripheral rim 16a of the body 2 in opposite directions towards the diametrically opposed corner portion, thereby opening the container. Alternatively once the seal has been broken by pushing lug 60 downwardly and lug 62 upwardly and the lid is lifted away from the body 2 at one corner portion, a similar operation can be performed at the diagonally opposite corner portion to disengage the lid from the body at both corner portions and hence the lid may be lifted away from the body.

The two sets of lugs 60,62 at the diametrically opposed corner portions provide opening from either of the two corner portions and also provide easy holding points for the container and which is again of value in stressful situations as may arise with combat injuries.

When the bandage is to be used in sterilised hospital or operating theatre situations, the container may be inverted prior to opening so that when opened the body 2 may be removed away from the lid 12 and the lid is used 12 as a tray support for the bandage on the donut formation 40 from which it can be easily removed by the surgeon or nursing staff by use of sterilised tweezers or forceps.

Although it is particularly advantageous for the container to be used during the manufacture of the bandage with the container body acting as a mould within which the bandage is built up by a deposition process, it is within the scope of the invention for the bandage to be fabricated externally of the container and then transferred into the container for packaging immediately after freeze drying. In that case, the legs 22 and associated structure for providing the partially open position of the lid can be omitted.

Although the container described herein has particular applicability for the packaging and preferably also the manufacture of a haemostatic bandage, the container also has applicability for other pharmaceutical products, particularly pharmaceutical products of high value and of possibly brittle or fragile structure, and which may be subject to post-dispensing treatment such as heat treatment, sterilisation or viral inactivation.

Although the container particularly described is of generally rectangular configuration, in other embodiments, the container may be of different configuration, such as circular. It is also to be understood that the present invention is not restricted to the embodiment described and modifications are possible within the scope of the present invention.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

The reference to any prior art in this specification is not, and should not be taken as, an acknowledgment or any form of suggestion that that prior art forms part of the common general knowledge.

What is claimed is:

1. A container comprising:
   a body; and
   a lid for closing the container to hermetically seal a product therein, said lid having a sealing rim including a layer of elastomeric material which sealingly engages with a sealing rim of the container body, and said elastomeric sealing material extending into the interior of the container beneath the lid to provide an elastomeric formation operative to engage an upper surface of the product within the container so as to apply a resilient bias thereto to hold a lower face of the product against the base of the container.

2. A container according to claim 1, wherein the sealing engagement provides a first, static, seal and a second, dynamic, seal.

3. A container according to claim 2, wherein the static seal provides a locking action to releasably lock the lid to the sealing rim of the container body.

4. A container according to claim 1, wherein the sealing rim of the lid is of inverted channel section to which the layer of elastomeric material is applied, the elastomeric layer including a formation which engages against a formation on the sealing rim of the container body to provide therewith a static seal and the elastomeric layer also having a lip to slidingly engage a surface of the sealing rim of the container to provide a dynamic seal.

5. A container according to claim 4, wherein the lip forming the dynamic seal slidably engages an inner surface of the sealing rim of the container body.

6. A container according to claim 5, wherein the formation providing the static seal is an inwardly directed lip lockably and sealingly engageable with an outwardly directed lip on the sealing rim of the container body.

7. A container according to claim 4, wherein a further sealing zone is formed between an upper end edge of the sealing rim of the container body and the immediately adjacent part of the elastomeric layer.

8. A container according to claim 1, wherein the container body has a lateral flange extending outwardly from its peripheral wall beneath the sealing rim and the flange is bordered externally over at least a substantial part of its periphery by an upstanding outer rim, said flange serving to stiffen the sealing rim to inhibit deformation thereof and degradation of the sealing effect, and said outer rim acting to shield the outer edge portion of the lid when it is in its fully closed position against accidental opening of the container.

9. A container according to claim 1, wherein the container is of approximately rectangular shape and opening of the container is effected by a set of first and second co-operating lugs at one of the corner portions of the container, the first lug forming part of the lid and the second lug forming part of the container body with the two cooperating lugs being side by side such that opening can be effected by lifting the first lug while pushing down on the second lug.

10. A container according to claim 1 having a facility to effect pressure relief within the interior of the container when hermetically sealed whereby to compensate for pressure variation over a temperature range to embrace sterilisation temperatures and freezing temperatures.

11. A container according to claim 1 for containing a product which is at least partially manufactured within the container by being subject at least to freeze drying within the container, wherein to facilitate freeze drying the lid is able to be applied to the container body but not fully sealed thereto to thereby permit the withdrawal of moisture during freeze drying.

12. A container according to claim 11, wherein the container includes means for releasably locking the lid in a first position with its sealing rim raised from the sealing rim of the container body sufficient to enable withdrawal of moisture from the interior of the container during freeze drying.

13. A container according to claim 12, wherein in said first position the sealing rim of the lid is uniformly spaced above the sealing rim of the container body such that after freeze drying has been completed the lid can be pushed downwardly to release the locking force and to move its sealing rim downwardly into sealing engagement with the sealing rim of the body, or the container body is able to be moved upwardly relative to the lid to achieve that effect.

14. A container according to claim 13, wherein the lid is releasably retained in its freeze drying position by releasable locking lugs such that upon release of the locking effect provided thereby, the lugs also act to guide the lid into its hermetically sealed position.

15. A container according to claim 11, wherein to facilitate freeze drying, the lid has a part in sealing relation to the body with another part of the lid being in a position to permit escape of moisture, and when drying is complete that latter part can then be moved into a position in which the container is hermetically sealed.

16. A container according to claim 11, wherein to provide effective heat transfer during freeze drying the outer surface of the container base is substantially planar to achieve large area surface contact with the surface of a freezing shelf of a freeze drier.

17. A container comprising:
   a body; and
   a lid for closing the container to hermetically seal a product therein, said lid having a sealing rim including a layer of elastomeric material which sealingly engages with a sealing rim of the container body, the sealing engagement providing a first, static, seal and a second, dynamic, seal and said elastomeric sealing material extending into the interior of the container beneath the lid to provide an elastomeric formation operative to engage an upper surface of the product within the container so as to apply a resilient bias thereto to hold a lower face of the product against the base of the container, wherein the elastomeric formation acts to inhibit movement of the product within the container, and the elastomeric formation flexes to accommodate a range of product thicknesses and/or surface irregularities.

18. A container according to claim 17, wherein the elastomeric formation is annular.

19. A container according to claim 17, wherein the container body has a lateral flange extending outwardly from its peripheral wall beneath the sealing rim and the flange is bordered externally over at least a substantial part of its periphery by an upstanding outer rim, said flange serving to stiffen the sealing rim to inhibit deformation thereof and degradation of the sealing effect, and said outer rim acting to shield the outer edge portion of the lid when it is in its fully closed position against accidental opening of the container.

20. A container according to claim 17, having a facility to effect pressure relief within the interior of the container when hermetically sealed whereby to compensate for pressure variation over a temperature range to embrace sterilisation temperatures and freezing temperatures, wherein the pressure relief facility is provided by a deformable wall portion of at least one of the body and lid.

21. A container according to claim 20, wherein the deformable wall portion is provided in the lid and comprises a bellows-like flexible wall structure in the lid.

22. A container for a pharmaceutical product to protect the product against physical damage, said container comprising a body for housing the product and a lid for closing the container to provide a hermetically sealed enclosure for the product therein, said container having a facility for providing internal pressure relief over a range of temperatures encompassing freezing to sterilizing to permit maintenance of the hermetic seal throughout the freezing to sterilizing temperatures to which the container will be exposed wherein the body and lid comprise a robust semi-rigid polymer of pharmaceutical grade and wherein the hermetic seal between co-operating parts of the body and lid is formed by an elastomeric layer therebetween wherein the elastomeric layer is applied to a peripheral rim of the lid to sealingly co-operate with a peripheral sealing rim of the body wherein the sealing co-operation between the elastomeric layer and the sealing rim of the body provides a first, static, seal and a second, dynamic, seal and wherein the elastomeric sealing layer applied to the lid extends inwardly of a sealing zone into the interior of the container beneath the lid to provide a resilient formation to engage the product within the container and apply a resilient bias thereto in a direction towards an opposing base of the container so as to urge the product against the base and thereby to maintain the product against movement within the container.

23. A container according to claim 22, wherein the pressure relief facility is provided by a deformable wall portion at least one of the container body and lid.

24. A container according to claim 23, wherein the deformable wall portion is provided in the lid and comprises a bellows flexible wall structure in the lid.

25. A container according to claim 23, wherein the range over which the pressure relief facility is effective includes 150° C.

26. A container according to claim 22, wherein the static seal provides a locking action to releasably lock the lid to the sealing rim of the container body.

27. A container according to claim 22, wherein the resilient formation acts to inhibit movement of the product within the container, and the resilient formation flexes to accommodate at least one of a range of product thicknesses and surface irregularities.

28. A container according to claim 27, wherein the resilient formation is annular.

29. A container according to claim 22, for containing a product which is at least partially manufactured within the container by being subject at least to freeze drying within the container, wherein to facilitate freeze drying the lid is able to be applied to the container body but not fully sealed thereto to thereby permit the withdrawal of moisture during freeze drying.

30. A container according to claim 29, wherein the container includes means for releasably locking the lid in a first position with its sealing rim raised from the sealing rim of the container body sufficient to enable withdrawal of moisture from the interior of the container during freeze drying.

31. A container according to claim 30, wherein in said first position the sealing rim of the lid is uniformly spaced above the sealing rim of the container body such that after freeze drying has been completed the lid can be pushed downwardly to release the locking force and to move its sealing rim downwardly into sealing engagement with the sealing rim of the body, or the container body is able to be moved upwardly relative to the lid to achieve that effect.

32. A container according to claim 31, wherein the lid is releasably retained in its freeze drying position by releasable locking lugs such that upon release of the locking effect provided thereby, the lugs also act to guide the lid into its hermetically sealed position.

33. A container according to claim 29, wherein to facilitate freeze drying, the lid has a part in sealing relation to the body with another part of the lid being in a position to permit escape of moisture, and when drying is complete that latter part can then be moved into a position in which the container is hermetically sealed.

34. A container according to claim 29, wherein to provide effective heat transfer during freeze drying the outer surface of the container base is substantially planar to achieve large area surface contact with the surface of a freezing shelf of a freeze drier.

35. A container according to claim 29, wherein the container is of approximately rectangular shape and opening of the container is effected by a set of co-operating first and second lugs at one of the corner portions of the container, the first lug forming part of the lid and the second lug forming part of the container body with the two lugs being side by side such that opening can be effected by lifting the first lug while pushing down on the second lug.

36. A container according to claim 35, wherein a second set of co-operating first and second lugs is also provided at the diagonally opposite corner portion.

37. A container for a pharmaceutical product to protect the product against physical damage, said container comprising a body for housing the product and a lid for closing the container to provide a hermetically sealed enclosure for the product therein, said container having a facility for providing internal pressure relief over a range of temperatures encompassing freezing to sterilizing to permit maintenance of the hermetic seal throughout the freezing to sterilizing temperatures to which the container will be exposed and wherein the body and lid comprise a robust semi-rigid polymer of pharmaceutical grade and wherein the hermetic seal between co-operating parts of the body and lid is formed by an elastomeric layer therebetween and wherein the elastomeric layer is applied to a peripheral rim of the lid to sealingly co-operate with a peripheral sealing rim of the body and wherein the sealing rim of the lid is of inverted channel section to which the layer of elastomeric material is applied, the elastomeric layer including a formation which engages against a formation on the sealing rim of the container body to provide therewith a static seal and the elastomeric layer also having a lip to slidingly engage a surface of the sealing rim of the container body to provide a dynamic seal.

38. A container according to claim 37, wherein the lip forming the dynamic seal slidably engages an inner surface of the sealing rim of the container body.

39. A container according to claim 38, wherein the formation providing the static seal is an inwardly directed lip lockably and sealingly engageable with an outwardly directed lip on the sealing rim of the container body.

40. A container according to 39, wherein a further sealing zone is formed between an upper end edge of the sealing rim of the container body and the immediately adjacent part of the elastomeric layer.

41. A container for a pharmaceutical product to protect the product against physical damage, said container comprising a body for housing the product and a lid for closing the container to provide a hermetically sealed enclosure for the product therein, said container having a facility for providing internal pressure relief over a range of temperatures encompassing freezing to sterilizing to permit maintenance of the hermetic seal throughout the freezing to sterilizing temperatures to which the container will be exposed and wherein the body and lid comprise a robust semi-rigid polymer of pharmaceutical grade and wherein the hermetic seal between co-operating parts of the body and lid is formed by an elastomeric layer therebetween and wherein the elastomeric layer is applied to a peripheral rim of the lid to sealingly co-operate with a peripheral sealing rim of the body and wherein the container body has a lateral flange extending outwardly from its peripheral wall beneath the sealing rim and the flange is bordered externally over at least a substantial part of its periphery by an upstanding outer rim, said flange serving to stiffen the sealing rim to inhibit deformation thereof and degradation of the sealing effect, and said outer rim acting to shield the outer edge portion of the lid when it is in its frilly closed position against accidental opening of the container.

* * * * *

UNITED STATES PATENT AND TRADEMARK OFFICE
CERTIFICATE OF CORRECTION

PATENT NO. : 7,114,617 B2 Page 1 of 1
APPLICATION NO. : 10/612766
DATED : October 3, 2006
INVENTOR(S) : Yewdall et al.

It is certified that error appears in the above-identified patent and that said Letters Patent is hereby corrected as shown below:

TITLE PAGE

Item (73) delete "Parkville" insert --Parkville, Victoria--

COLUMN 14

Line 40, delete "claim 29" and enter --claim 22--

COLUMN 16

Line 16, delete "frilly" and insert --fully--

Signed and Sealed this

Sixth Day of March, 2007

JON W. DUDAS
*Director of the United States Patent and Trademark Office*